United States Patent

Plant Pat. 3,929

Patented June 29, 1976

3,929

GRAPEVINE

Harold P. Olmo, Davis, Calif., assignor to The Regents of the University of California, Berkeley, Calif.

Filed May 15, 1975, Ser. No. 577,974

Int. Cl.[2] A01H 5/03

U.S. Cl. Plt.—47 1 Claim

This invention relates to a new and distinct variety of grapevine of the vinifera species to be used for the production of red table wine of Cabernet type.

The new variety is the result of a cross of F2–7 (Carignane × Cabernet-Sauvignon) × Merlot, made in 1946 at The University of California vineyard at Davis, Calif. The seedling M–51–50 was selected as the most promising in a population of 363 seedling vines first fruited at Davis, Calif., in 1951.

The first fruit sample harvested on Sept. 21, 1951, tested 25.6° Balling with a total acid (as tartaric) of 0.73 percent; in 1952 harvest was on September 19 at 19.6° Balling and 0.86 acid. The small wine tests indicated outstanding quality with accentuation of the Cabernet flavor and aroma.

It has been multiplied asexually by budding or grafting and has retained the characteristics of the original plant. It has been tested as Selection 802 under commercial vineyard conditions in trial plots at Oakville (since 1960), Modesto and Fresno (since 1966), Calif.

The Cabernet-Sauvignon is considered to be one of the best red wine grapes and is world renowned as a base of the finest Bordeaux clarets. In California no other variety has surpassed its reputation for high quality. The variety has some faults: a rampant and bushy growth habit making pruning difficult, small loose clusters and berries that reduce wine yield and call for long (cane) pruning, and late maturity of the fruit. The young wine is harsh and rough thus requiring a long period of aging in cask and bottle to achieve perfection. The characteristic flavor of the fruit is very variable from season to season depending on locality and microclimate, a capriciousness that follows in the bouquet and quality of the aged wine. The variety lacks flavor and acidity in warmer climates and then produces mediocre wines.

The objectives in breeding this new variety were to overcome some of the cultural faults; to increase cluster and berry size and fruitfulness, to advance the ripening period and accentuate the characteristic flavor and aroma of the wine, to produce wider adaptation to climate.

This new variety is very widely adapted from the cooler coastal regions of California where premium wines are produced, to areas as warm as Fresno, Calif. The wine closely resembles Cabernet-Sauvignon but has even more flavor and aroma. The yield is higher than the Cabernet-Sauvignon and the fruit ripens earlier. Early ripening is an important advantage in some seasons. It is a premium wine that improves with aging and has an exceptionally long life. The vine has a better growth habit than Cabernet-Sauvignon but has even more flavor and aroma. The yield is higher than the Cabernet-Sauvignon and the fruit ripens earlier. Early ripening is an important advantage in some seasons. It is a premium wine that improves with aging and has an exceptionally long life. The vine has a better growth habit than Cabernet-Sauvignon and allows easier pruning and harvest.

The varietal characteristics of the novel plant described below in detail were observed during the first fruiting season and thereafter during its testing in trial plots at Oakville, Modesto and Fresno, Calif.

The vine—Of medium vigor; upright in growth habit with few canes, similar to Carignane, trunk thick, easily trained and pruned, more fruitful than Cabernet-Sauvignon and productive when short pruned.

Shoot tip—(10″–12″). Straight, leafy, very short basal internodes, unfolding leaves with pinkish borders, slight arachnoid hairiness, soon becomes glabrous, flower clusters on nodes 2 and 3.

Figure 1:
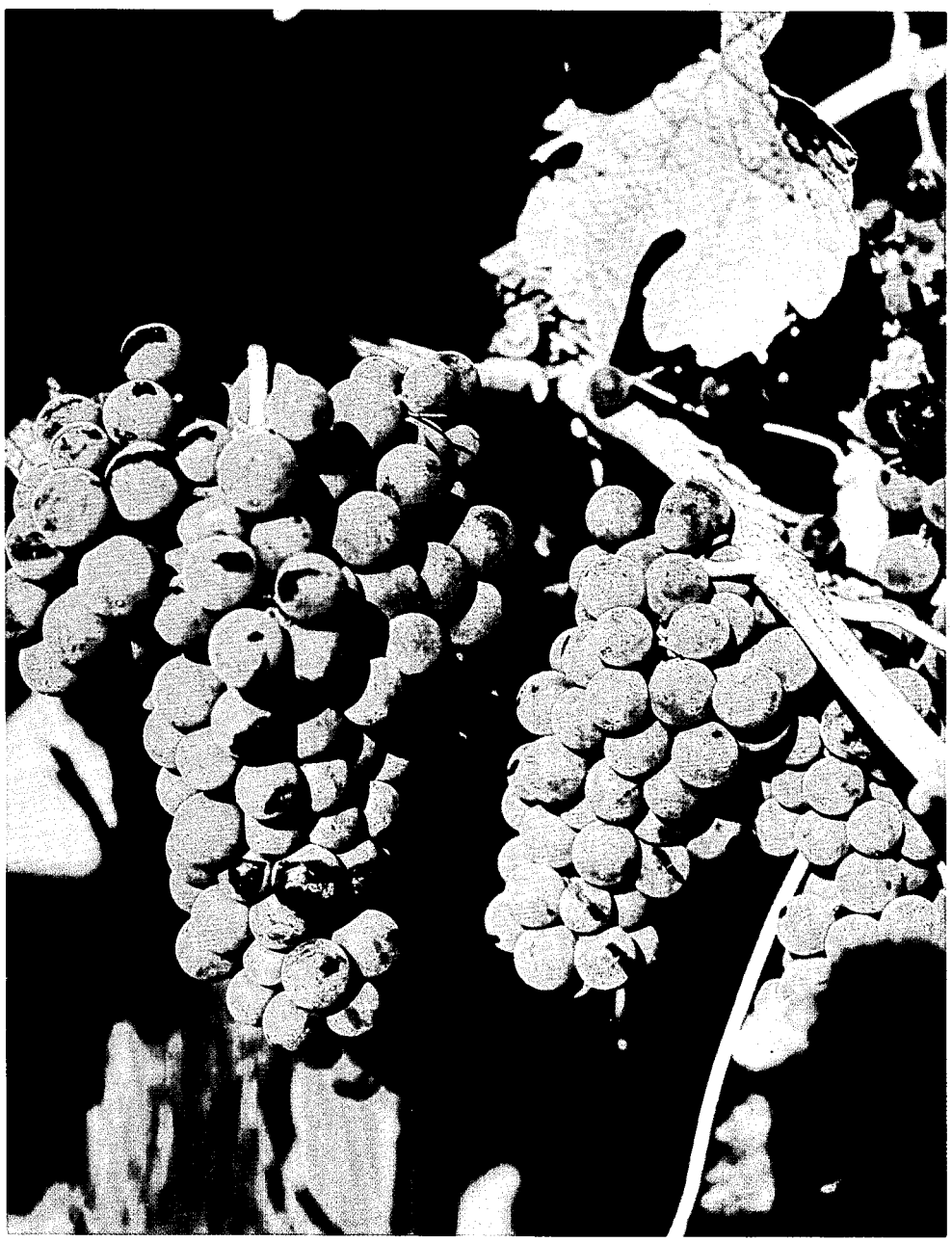
FIG. 1 is a view of a typical cluster and stem of the new variety.
Figure 2:
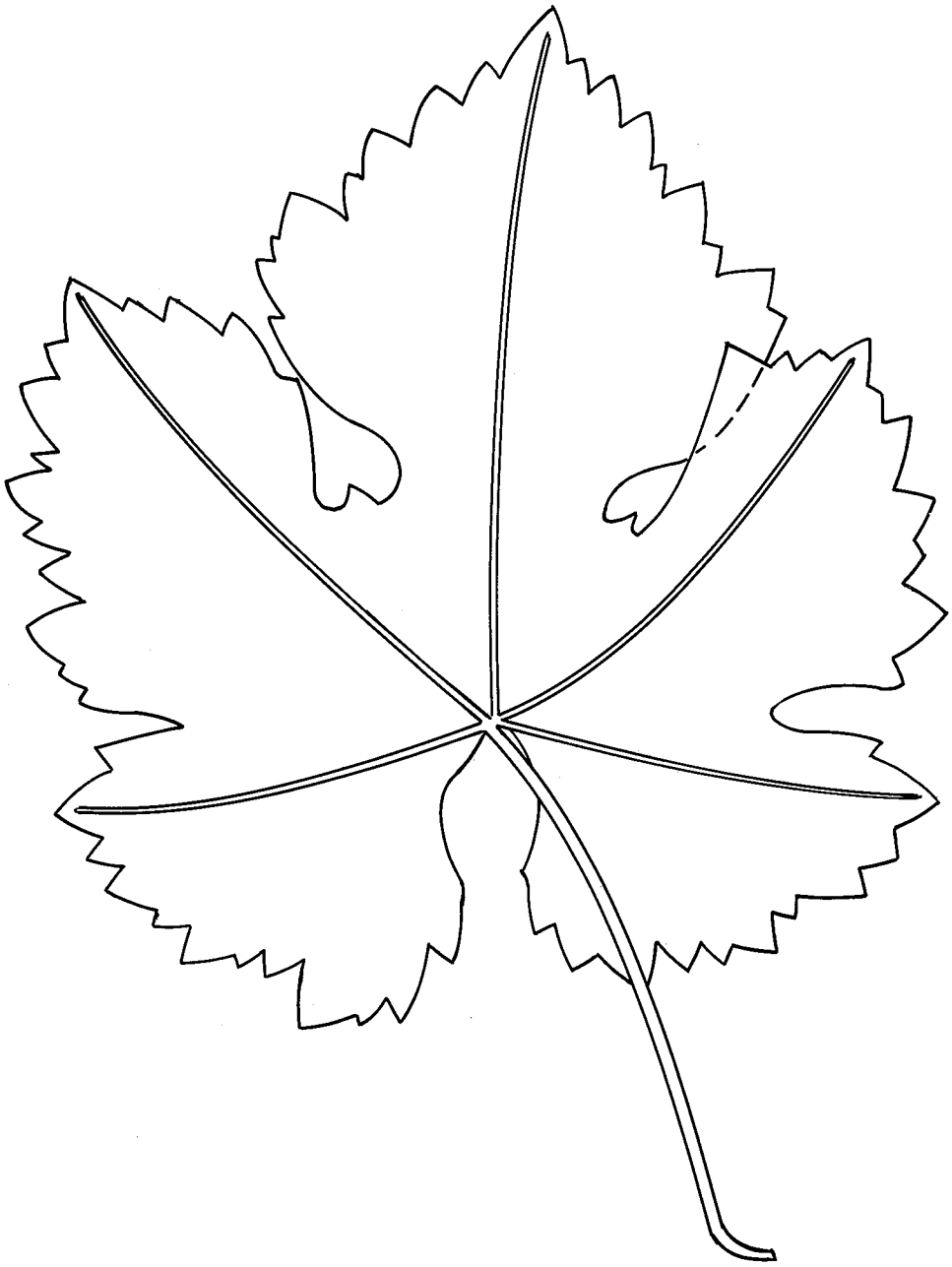
FIG. 2 illustrates in outline form a typical leaf of the new variety.

Leaf—(see FIG. 2). The leaf is dark green, completely glabrous, cuneiform in outline, of thin papery texture, deeply lobed; upper sinuses very deep, with bases broad and often interrupted with a large tooth, closed at mid-depth by overlapping lobes; central lobe spear shaped, triangular, terminating in large acute and sharp apex; lateral lobes prominent and outer margins parallel, elongated much beyond the general outline; lower sinuses shallow but opened wide at base, almost closed at neck; teeth large, in two series, equilateral, sides rounded with mucronate tips; petiolar sinus deep, very wide, fully open, wide U-shaped to lyre-shaped; cut to vein near base; ribs very slender but raised in relief on underside of blade, suffused wine-red near petiole; petiole slender, rounded, very long, completed suffused with wine-red color; fall coloration orange with later wine-red splotching, time of leaf fall medium, before Cabernet-Sauvignon.

Canes—Short, base thick, unbranched; the basal internodes shortened, striated with dark brown bands.

The cluster—The cluster is short conical, 11.6 cm. x 14.5 cm., averages 267 g., variable in fruit set from loose to very compact but usually well-filled; the main rachis bears an average of 161 berries; shoulder development in about half of clusters bearing another 39 berries; the cluster stem lignified and brown to where it first bends at a right angle about 1.6 cm. from attachment to the cane, thence extending downward another 2.2 cm. to the point of cluster branching, medium thick, 6 mm. in diameter, tough and difficult to cut. Clusters usually two per cane, borne close to the base and crowded in the head of the vine.

Berry spherical, average weight of 10 largest berries per cluster 19 9., relatively uniform in size from base to apex of cluster, black with bluish bloom, similar to Cabernet-Sauvignon in skin and pulp texture and color, usually two or three seeds per berry.

The fruit reaches commercial maturity for dry table wine one or two weeks in advance of the Cabernet-Sauvignon, it holds well on the vine without shriveling or spoilage, retaining the typical Cabernet flavor much later in the season than the Cabernet-Sauvignon.

The variety—The most distinctive feature of the variety is the accentuated Cabernet flavor present in the fresh fruit. When vinified, a table wine very similar to the Cabernet-Sauvignon is produced, capable of long aging and reaching very high quality. The vine has larger berries and clusters, is more fruitful and earlier ripening than the Cabernet-Sauvignon. This new variety has a wider range of climatic adaptability than other Cabernet varieties now grown, and is easier to train and prune.

I claim:

1. The new and distinct variety of grapevine herein described and illustrated and identified by the characteristics enumerated above.

No references cited.

ROBERT E. BAGWILL, Primary Examiner